US006916290B2

(12) United States Patent
Hedengren et al.

(10) Patent No.: US 6,916,290 B2
(45) Date of Patent: Jul. 12, 2005

(54) IN SITU TUMOR TEMPERATURE PROFILE MEASURING PROBE AND METHOD

(75) Inventors: Kristina Helena Valborg Hedengren, Schenectady, NY (US); William Paul Kornrumpf, Schenectady, NY (US); Mark Lloyd Miller, Schenectady, NY (US); Egidijus Edward Uzgiris, Schenectady, NY (US)

(73) Assignee: General Electric Company, Niskayuna, NY (US)

(*) Notice: Subject to any disclaimer, the term of this patent is extended or adjusted under 35 U.S.C. 154(b) by 51 days.

(21) Appl. No.: 10/090,576

(22) Filed: Mar. 5, 2002

(65) Prior Publication Data

US 2002/0099304 A1 Jul. 25, 2002

Related U.S. Application Data

(62) Division of application No. 09/635,463, filed on Aug. 11, 2000, now Pat. No. 6,419,635.

(51) Int. Cl.[7] .............................. A61B 5/00; G01K 7/00
(52) U.S. Cl. ........................................ 600/549; 374/166
(58) Field of Search ................................ 600/549, 551; 374/163–166

(56) References Cited

U.S. PATENT DOCUMENTS

| | | | | |
|---|---|---|---|---|
| 4,397,314 A | * | 8/1983 | Vaguine | 600/549 |
| 4,665,927 A | * | 5/1987 | Daily | 600/549 |
| 4,960,109 A | | 10/1990 | Lele | |
| 5,226,426 A | * | 7/1993 | Yoon | 600/566 |
| 6,086,247 A | * | 7/2000 | von Hollen | 600/549 |
| 6,117,088 A | | 9/2000 | Kreizman et al. | |
| 6,162,184 A | * | 12/2000 | Swanson et al. | 600/549 |
| 6,419,635 B1 | * | 7/2002 | Hedengren et al. | 600/549 |
| 6,511,478 B1 | * | 1/2003 | Burnside et al. | 606/41 |

* cited by examiner

Primary Examiner—Max F. Hindenburg
Assistant Examiner—Jonathan Foreman
(74) Attorney, Agent, or Firm—Jean K. Testa; Christian G. Cabou

(57) ABSTRACT

An in situ breast tumor temperature profile measuring probe includes a rod, thermal sensors and electrical output leads. The thermal sensors are formed in spaced apart holes in an outer insulating layer of the rod and a common electrical input lead to provide an electrical input signal to the thermal sensors is disposed below and has portions exposed at the holes and electrically connected to the thermal sensors. The thermal sensors receive the electrical input signal from the common electrical input lead, sense the temperature of biological matter adjacent to the thermal sensors and produce an electrical output signal correlated thereto. Each electrical output lead mounted to the outer insulating layer is in electrical contact with a different one of the thermal sensors to receive the electrical output signal from the one thermal sensor and output the same.

9 Claims, 4 Drawing Sheets

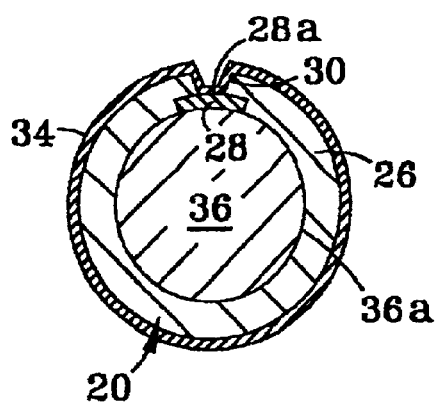
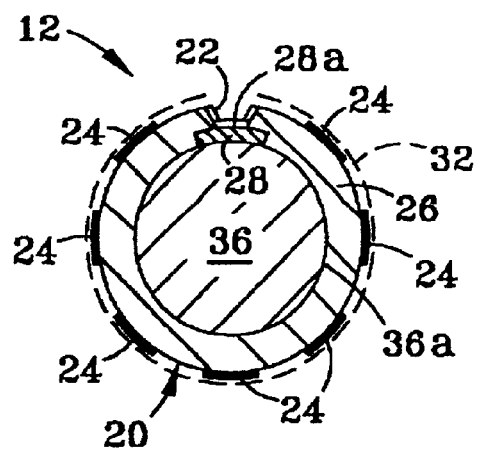
FIG. 8  FIG. 9
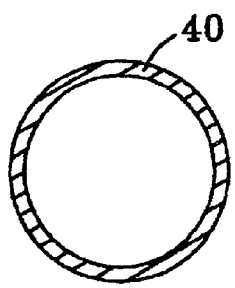
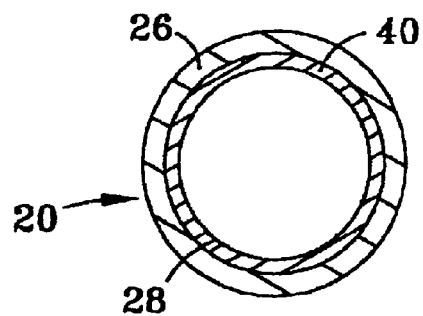
FIG. 10  FIG. 11
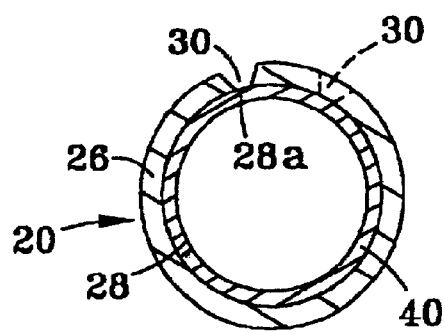
FIG. 12

IN SITU TUMOR TEMPERATURE PROFILE MEASURING PROBE AND METHOD

This application is a division application for Ser. No. 09/635,463, filed Aug. 11, 2000 in the U.S. Patent and Trademark Office, now issued as U.S. Pat. No. 6,419,635, which is hereby incorporated by reference in its entirety.

BACKGROUND OF THE INVENTION

The present invention generally relates to breast tumor screening devices and methods and, more particularly, is concerned with an in situ tumor temperature profile measuring probe and a method of using the probe.

The early detection of tumors, which is the principal strategy for reducing the mortality of breast cancer, is a challenging task. X-ray mammograms, widely used for mass screening, cannot reliably detect early tumors much below 1 cm in size. The false negative rate is 5 to 15% for tumors of palpable size. Mammography is inconclusive in differentiating malignant tumors from nonmalignant breast disease, such as harmless cysts and benign fibroid tissue. Ultrasound, which is commonly used to discriminate between tumor masses and cysts after indications are found with mammography, does not have the sensitivity to detect very small invasive tumors. Magnetic resonance (MR) imaging lacks sensitivity and specificity. With MR dynamic contrast methods, sensitivity is high but the specificity is not high enough to reliably resolve benign from cancerous lesions. Histo-pathological findings from biopsies are the only reliable means of breast cancer diagnosis and, consequently, many women are subjected to biopsies to improve their chances for long-term survival if any abnormality is found.

Angiogenesis is the growth of new blood vessels from existing capillaries. It is a fundamental process of tumor growth and metastasis. All solid tumors require angiogenesis for growth. This process has received much attention since it was first postulated in 1971. In breast cancer, it has been shown that the level of angiogenesis as defined by microvessel density has prognostic value. Studies have shown that the levels of angiogenesis in breast cancer are correlated with the potential for metastasis and aggressive growth. The angiogenic switch occurs early in tumor growth. A method that is sensitive to increased blood perfusion in a suspected lesion would be of value for early detection of breast cancer.

Tumors have a higher temperature than surrounding tissue by virtue of increased blood circulation in the tumor, particularly in the peripheral region of the tumor. Increased perfusion of arterial blood could set up a temperature gradient from the tumor interior to the surrounding tissue. It is believed that excess tumor temperature could also arise from the higher metabolic rates of growing tumor cells. This temperature excess has been visualized by surface thermography in the case of large tumors near the surface of the breast, though surface infrared thermography in clinical practice became controversial for a number of technical reasons.

It appears that no reliable or accepted data are available on the characteristics of tumor temperatures by other imaging methods or by in situ methods. In the former case, magnetic resonance (MR) imaging cannot produce an ab initio temperature map of tissue due to the variations of phase or frequency caused by variations in susceptibility of tissue. In the latter case, single-point temperature measurements are subject to considerable error due to heat conduction effects of the sensor itself and of unknown temperature gradients in the tissue. In situ probes for internal temperature must satisfy rigorous requirements on conduction of heat and thermal mass and must be capable of sensing small temperature gradients reliably. Tumor temperatures can only be inferred from non-invasive surface thermography images and, thus, are limited in sensitivity, resolution and accuracy.

Because current imaging modalities cannot completely identify all cancerous lesions, many biopsy procedures are performed. Surgical biopsy procedures are particularly expensive and uncomfortable to patients. The lesion is visualized and a localizing guide wire is placed through a small needle into the lesion. The needle is removed. The guide wire is left in place. The patient is taken to surgery for the surgical biopsy procedure in which the wire localizes the lesion center for the surgeons. A reduction of such procedures would be desirable. Other common biopsy procedures for the breast involve less invasive needle methods with vacuum aspiration.

The inventors herein have recognized the desirability of having a temperature probe that could be used to provide added information to radiologists and which would be helpful in avoiding more severe forms of biopsy procedures. However, problems exist with current temperature probes which are found in the prior art. Current temperature probes are relatively large. The smallest conventional thermocouple wires are about 120 micrometers in diameter and are very fragile. Two such wires are needed for each probe element. The thermal conductivity of the wires in these relatively large probes affects the temperature measurements made by the probe with the result being that the probe does not measure tumor temperatures with high accuracy.

Consequently, a need remains for a tumor temperature probe which is smaller in size than prior art probes and can provide reliable and sensitive temperature measurements and thus would overcome the aforementioned problems of the prior art probes, without introducing any new problems in place thereof.

BRIEF SUMMARY OF THE INVENTION

The present invention provides an in situ breast tumor temperature profile measuring probe and a method of using the probe which are designed to satisfy the aforementioned need. The in situ tumor temperature profile measuring probe of the present invention is relatively small in size and does not produce a level of thermal conductivity that would affect the temperature measurements made by the measuring probe. The measuring probe has an array of temperature sensors, being microscopic in size, that will be able to detect and thus provide a profile of temperatures of a breast tumor and surrounding tissue with high accuracy. The measuring probe may be used with standard breast biopsy procedures and is capable of measuring small temperature differences in and around breast tumors so as to enable the diagnosis of cancer at an early stage when the tumor is small in size. The measuring probe thus will fulfill the need for a suitable temperature probe which would provide added information to radiologists and may be helpful in avoiding more severe forms of biopsy procedures.

In one embodiment of the present invention, an in situ tumor temperature profile measuring probe is provided which comprises: an elongated rod including a pair of opposite end portions, an outer insulating layer having a plurality of spaced apart holes defined therein at one of the opposite end portions of the rod, and a common electrical input lead extending between the opposite end portions of the rod and disposed below the holes and having portions exposed at the holes, the common electrical input lead being adapted to provide an electrical input signal; a plurality of spaced apart thermal sensors each formed within one of the holes of and on the outer insulating layer of the rod in electrical contact with the common electrical input lead of the rod, each thermal sensor being adapted to receive the electrical input signal from the common electrical input lead, sense the temperature of biological matter adjacent to where the thermal sensor is placed and produce an electrical output signal correlated to the temperature sensed; and a plurality of electrical output leads each mounted to the outer insulating layer of the rod in electrical contact with a different one of the thermal sensors and extending to the other of the opposite end portions of the rod, each of the electrical output leads being adapted to receive the electrical output signal from the one of the thermal sensors and output the electrical output signal to means for collecting the output signals and forming a temperature profile of the biological matter.

More particularly, the common electrical input lead of the rod is either a hollow tube or an elongated strip, each made of an electrically conductive material. The holes and thermal sensors therein are arranged in either a linear array in which the thermal sensors are aligned axially with one another along the rod or a staggered array in which the thermal sensors are offset circumferentially and axially from one another about and along the rod. Each thermal sensor and each electrical output lead are microscopic, or micron-scale, in size. The probe further comprises an exterior insulating layer covering at least the electrical output leads.

In another exemplary embodiment of the present invention, an in situ tumor temperature profile measuring probe assembly is provided which comprises: the above-defined measuring probe; a hollow needle being insertable into biological matter and having opposite ends and an interior passageway defined through the hollow needle which are open at each of the opposite ends thereof so as to adapt the hollow needle to receive the measuring probe through the interior passageway and guide the one end portion of the measuring probe into the biological matter; and an electrical connector for providing an interface between the electrical input and output leads of the measuring probe and a computer, the connector being adapted to receive the electrical output signals from the electrical output leads of the measuring probe and transmit the temperatures sensed by the thermal sensors of the measuring probe to the computer for collecting the output signals and forming a temperature profile of the biological matter.

In a further exemplary embodiment of the present invention, a method of measuring an in situ tumor temperature profile is provided which comprises the steps of: providing a common electrical input signal; receiving the common electrical input signal at spaced apart locations within biological matter; sensing temperatures of the biological matter at the spaced apart locations within the biological matter; producing a plurality of electrical output signals corresponding to the respective temperatures sensed; and transmitting the electrical output signals produced to a computer for collecting the output signals. The method also comprises the steps of forming a temperature profile of the biological matter and using the temperature profile of the biological matter to determine whether a tumor is present and what type of a tumor may exist in the biological matter.

BRIEF DESCRIPTION OF THE DRAWINGS

FIG. 8 is a cross-sectional view depicting a fifth step in the fabrication of the first embodiment of the measuring probe.

FIG. 9 is a cross-sectional view depicting a sixth step in the fabrication of the first embodiment of the measuring probe.

FIG. 10 is a cross-sectional view depicting a first step in the fabrication of a second embodiment of the measuring probe.

FIG. 11 is a cross-sectional view depicting a second step in the fabrication of the second embodiment of the measuring probe.

FIG. 12 is a cross-sectional view depicting a third step in the fabrication of the second embodiment of the measuring probe.

DETAILED DESCRIPTION OF THE INVENTION

Figure 1:
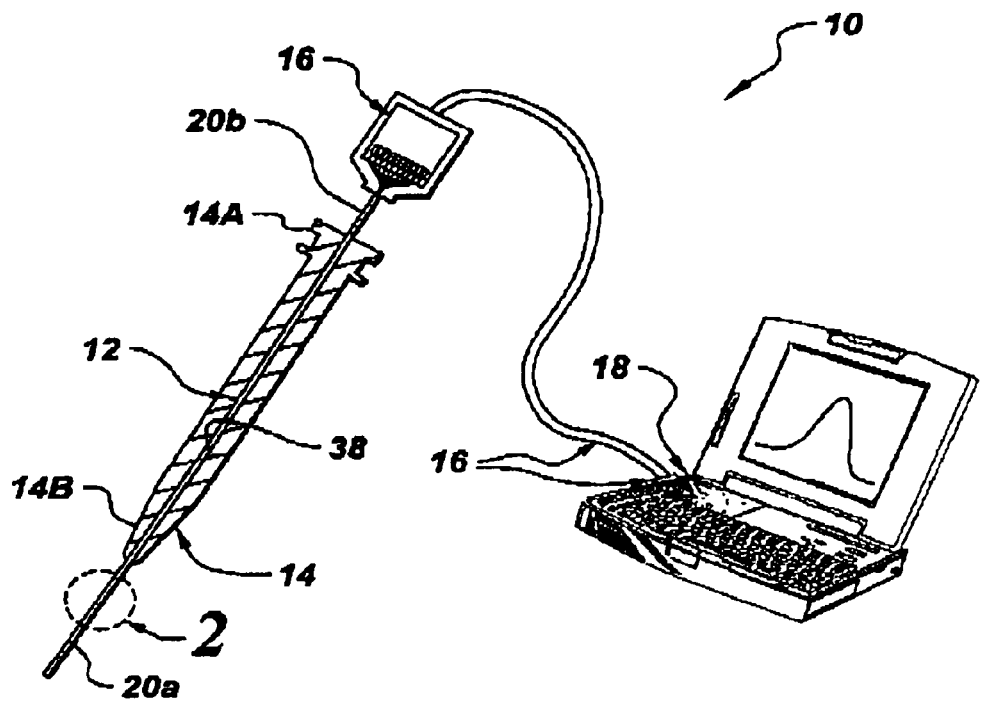
FIG. 1 is a perspective view of a probe, a hollow needle and a connector of an in situ breast tumor temperature profile measuring probe assembly of the present invention shown with a computer.
Figure 2:
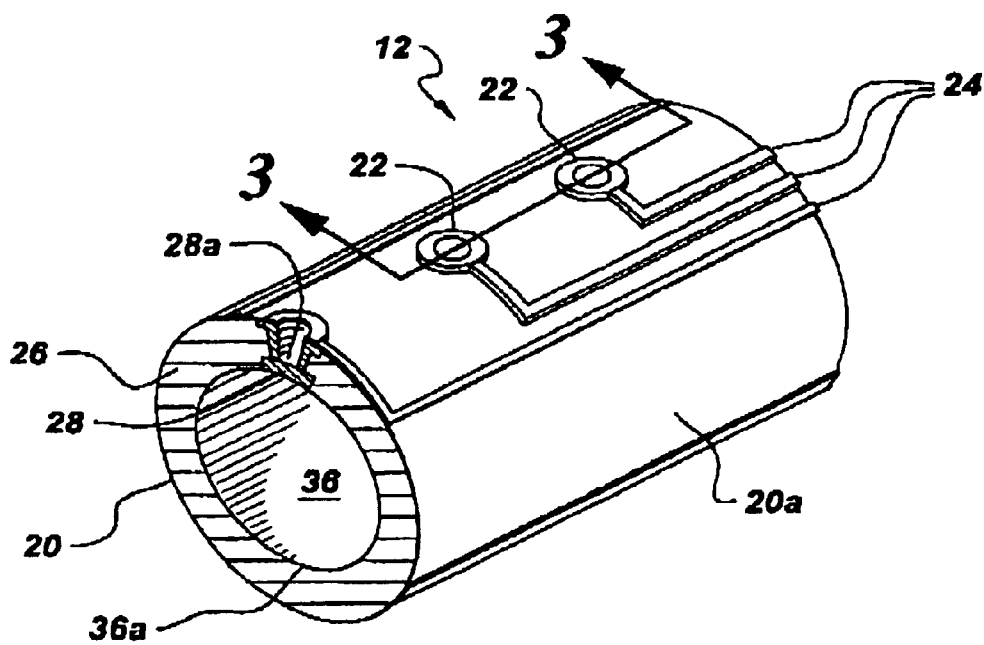
FIG. 2 is an enlarged detailed perspective view of the area of the in situ breast tumor temperature profile measuring probe of the present invention enclosed by circle 2 of FIG. 1.
Figure 3:
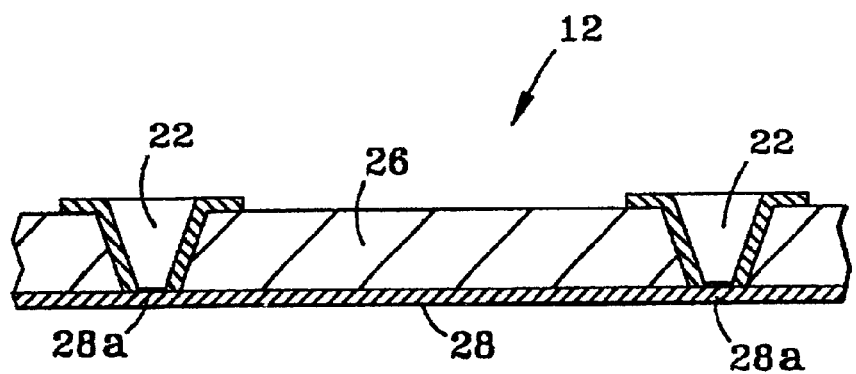
FIG. 3 is an enlarged longitudinal sectional view of the measuring probe taken along line 3—3 of FIG. 2 showing two thermal sensors of the probe.
Figure 14:
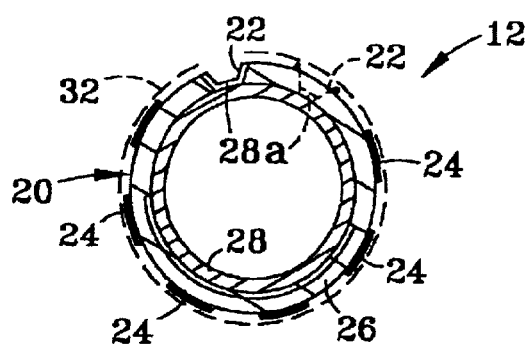
FIG. 14 is a cross-sectional view depicting a fifth step in the fabrication of the second embodiment of the measuring probe.

Referring now to the drawings and particularly to FIG. 1, there is illustrated an in situ breast tumor temperature profile measuring probe assembly, generally designated 10. The in situ breast tumor temperature profile measuring probe assembly 10 basically includes an in situ breast tumor temperature profile measuring probe 12 of the present invention, a hollow needle 14 and an electrical connector 16. The measuring probe 12 may have one of two embodiments. A cross-section of a first embodiment of the measuring probe 12 is shown in FIGS. 2 and 9 whereas a cross-section of a second embodiment of the measuring probe 12 is shown in FIG. 14. The probe assembly 10 is used with a computer 18 of any suitable conventional type to produce a temperature profile.

Referring now to FIGS. 2 to 14, the measuring probe 12 basically includes an elongated rod 20, a plurality of spaced apart thermal sensors 22 and a plurality of electrical output leads 24, in each of the embodiments of the measuring probe 12. The rod 20 has a pair of spaced apart opposite end portions 20a, 20b, an outer insulating layer 26 and a common electrical input lead 28 which provides an electrical input signal to the thermal sensors 22 when connected by the electrical connector 16 to the computer 18 or other suitable source. The outer insulating layer 26 of the rod 20 has a plurality of spaced apart holes 30 defined therethrough at the one end portion 20a of the rod 20. The common electrical input lead 28 of the rod 20 is disposed below the outer insulating layer 26 and extends between the opposite end portions 20a, 20b of the rod 20. Portions 28a of the common electrical input lead 28 are exposed at the holes 30 in the outer insulating layer 26. Each thermal sensor 22 is formed within one of the holes 30 of the rod 20 and on the outer insulating layer 26 thereof in electrical contact with one of the exposed portions 28a of the common electrical input lead 28. Each thermal sensor 22 has a substantially concave or cup-shaped configuration and is substantially U-shaped in cross section and is adapted to receive the electrical input signal from the common electrical input lead 28, to sense the temperature of biological matter adjacent to where the thermal sensor 22 is placed in the biological matter and to produce an electrical output signal correlated to the temperature sensed. Each electrical output lead 24 is mounted to the outer insulating layer 26 of the rod 20 in electrical contact with a different one of the thermal sensors 22 and extends therefrom to the other opposite end portion 20b of the rod 20. Each electrical output lead 24 is adapted to receive and output the electrical output signal from the different one of the thermal sensors 22 via the electrical connector 16 to the computer 18 for collecting the temperature data and forming the temperature profile of the biological matter. Each of the thermal sensors 22 and each of the electrical output leads 24 are microscopic or micron-scale in size to minimize the lateral thermal conductivity of probe 12 so that accurate temperature measurements are possible. For example, the electrical output leads can be 1 micrometer by 25 micrometers in cross-section. The measuring probe 12 also includes an exterior insulating layer 32 as shown in FIGS. 9 and 14. The exterior insulating layer 32 covers at least the electrical output leads 24 such that they do not interfere with the temperature of the biological matter sensed at the sites of the thermal sensors 22.

Referring to FIGS. 2 to 9, in the first embodiment of the measuring probe 12, the elongated rod 20 has a solid core 36. The solid core 36 of the rod 20 is made of a substantially electrically and thermally nonconducting or insulative material, such as Kevlar™, with a minimum diameter of 0.5 mm. The common electrical input lead 28 of the rod 20 is an elongated strip 28 made of a first electrically conductive material, such as constantan. The common electrical input lead 28 of the rod 20 is disposed on the exterior surface 36a of the solid core 36 of the rod 20. The thermal sensors 22 are arranged in a linear array in which they are aligned with respect to one another along the common electrical input lead 28 of the rod 20.

Figure 4:
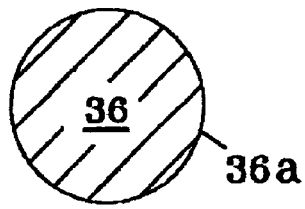
FIG. 4 is a cross-sectional view depicting a first step in the fabrication of a first embodiment of the measuring probe.
Figure 5:
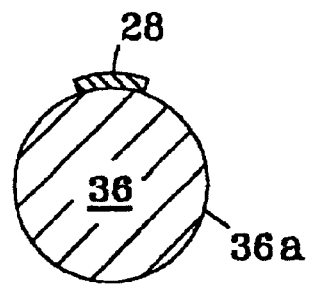
FIG. 5 is a cross-sectional view depicting a second step in the fabrication of the first embodiment of the measuring probe.
Figure 6:
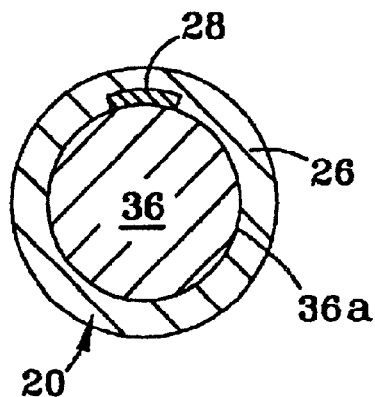
FIG. 6 is a cross-sectional view depicting a third step in the fabrication of the first embodiment of the measuring probe.
Figure 7:
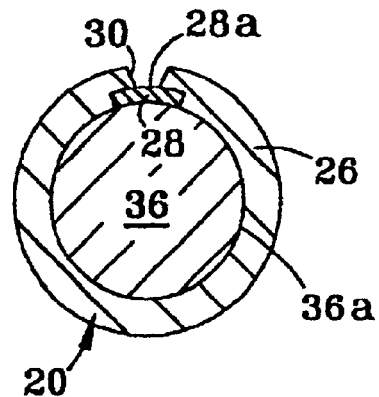
FIG. 7 is a cross-sectional view depicting a fourth step in the fabrication of the first embodiment of the measuring probe.

The first embodiment of the measuring probe 12 can be made by using microfabrication techniques which involve the series of steps as depicted in FIGS. 4 to 9. As shown in FIG. 4, in a first step the solid core 36 of the rod 20 is provided. As shown in FIG. 5, in a second step, the common electrical input lead 28 of the rod 20 is provided in the form of the elongated strip 28 of a first electrically conductive material, such as constantan, which is deposited on the exterior surface 36a of the solid core 36 of the rod 20. As shown in FIG. 6, in a third step, the first insulating layer 26 of the rod 20, being a suitable dielectric material, is deposited on the common electrical input lead 28 and the exterior surface 36a of the solid core 36. As shown in FIG. 7, in a fourth step, the spaced apart holes 30 in the linear array are made through the outer insulating layer 26 so as to expose portions 28a of the common electrical input lead 28. As shown in FIG. 8, in a fifth step, a second metal layer 34 of a second electrically conductive material, such as copper, is deposited on the outer insulating layer 26, in the holes 30 and on the exposed portions 28a of the common electrical input lead 28 of the rod 20. As shown in FIG. 9, in a sixth step, the second metal layer 34 is etched away or patterned so as to leave the thermal sensors 22 on the rod 20 and the electrical output leads 24 on the rod 20 extending from the thermal sensors 22 to the other opposite end 20b of the rod 20.

The thermal sensors 22 of the first embodiment provide thermocouple junctions between the common electrical input lead 28 and the plurality of electrical output leads 24 at the bottom of holes 30. In a final step, the exterior insulating layer 32, represented by a dashed line in FIG. 9, is applied over the outer insulating layer 26 so as to cover the electrical output leads 24 and the thermal sensors 22. Therefore, only the thermal sensors 22 are able to contact the biological material such that only the temperatures of the biological material at the sites of the thermal sensors 22 will be sensed and thus provide a signal at each of the electrical output leads 24 to correspond to the value of the temperature sensed at the respective site.

Figure 13:
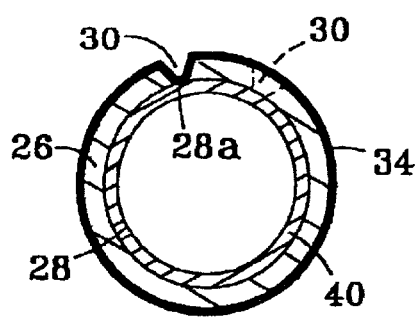
FIG. 13 is a cross-sectional view depicting a fourth step in the fabrication of the second embodiment of the measuring probe.

Referring to FIGS. 10 to 14, in the second embodiment of the measuring probe 12, the elongated rod 20 and the common electrical input lead 28 thereof are formed by a thin hollow tube made of a first electrically conductive material, such as constantan, and the thermal sensors are arranged in a circumferentially and axially staggered array with respect to one another about and along the common electrical input lead 28 of the rod 20. The second embodiment of the measuring probe 12 can be made by using microfabrication techniques which involve the series of steps as depicted in FIGS. 10 to 14. As shown in FIG. 10, in a first step, the common electrical input lead 28 and part of the elongated rod 20 are provided in the form of the electrically conductive hollow metallic tube 40, such as made of constantan. As shown in FIG. 11, in a second step, the outer insulating layer 26 of the rod 20, being a suitable dielectric, is deposited on the hollow metallic tube 40. As shown in FIG. 12, in a third step, the plurality of spaced apart holes 30 are made in the outer insulating layer 26 and expose the portions 28a of the common electrical input lead 28 across the bottoms of the holes 30. The spaced apart holes 30 are arranged in the circumferentially and axially staggered array with respect to with one another along and about the rod 20. As shown in FIG. 13, in a fourth step, a second metal layer 34, such as copper, is deposited on the outer insulating layer 26, within the holes 30 and on the exposed portions 28a of the common electrical input lead 28. As shown in FIG. 14, in a fifth step, the second metal layer 34 is etched away or patterned so as to leave and thus form the thermal sensors 22 and the electrical output leads 24 on the rod 20. As in the case of the first embodiment of the probe 12, the thermal sensors 22 in the second embodiment of the probe 12 provide thermocouple junctions between the common electrical input lead 28 and the plurality of electrical output leads 24. In a final step, the exterior insulating layer 32, represented by a dashed line in FIG. 14, is applied over the outer insulating layer 26 so as to cover the electrical output leads 24 and the thermal sensors 22. Thus, the thermal sensors 22 are able to contact the biological material such that only temperatures of the biological material at the sites of the thermal sensors 22 will be sensed and thus provide an electrical signal from the common electrical input lead 28 through the thermal sensors 22 to the electrical output leads 24 to correspond to the value of the temperature sensed at the respective site.

Referring again to FIG. 1, the hollow needle 14 of the assembly 10 is a standard type of clinical instrument similar to the type of hollow needle used in standard breast biopsy procedures. The hollow needle 14 has opposite ends 14A, 14B and an interior passageway 38 defined through the hollow needle 14 and being open at each of the opposite ends 14A, 14B.

In accordance with the method of the present invention for measuring an in situ breast tumor temperature profile, the hollow needle 14 is first inserted into the biological matter, such as into a breast tumor and/or surrounding tissue. The inserted hollow needle 14 either receives the measuring probe 12 or already has the measuring probe 12 inserted through the interior passageway 38 thereof. The needle 14 guides the one end portion 20a of the rod 20 of the measuring probe 12 into the biological matter. The hollow needle 14 is then retracted from the biological matter and along the measuring probe 12 whereupon the measuring probe 12 remains in contact with the biological matter with the thermal sensors 22 at known spaced apart locations or sites in the biological matter. The electrical connector 16 is then connected to the common electrical input lead 28 and the electrical output leads 24 at the other end portion 20b of the rod 20 of the measuring probe 12 to provide an interface between the electrical input and output leads 28, 24 of the measuring probe 12 and the computer 18. The electrical connector 16 receives the electrical output signals from the common electrical input leads 28 and the output leads 24 of the measuring probe 12 and transmits them to the computer 18 for collecting and processing the output signals and thus temperatures sensed at the sites of the thermal sensors 22 and forming a temperature profile of the biological matter based on the sensed temperatures.

Figure 15:
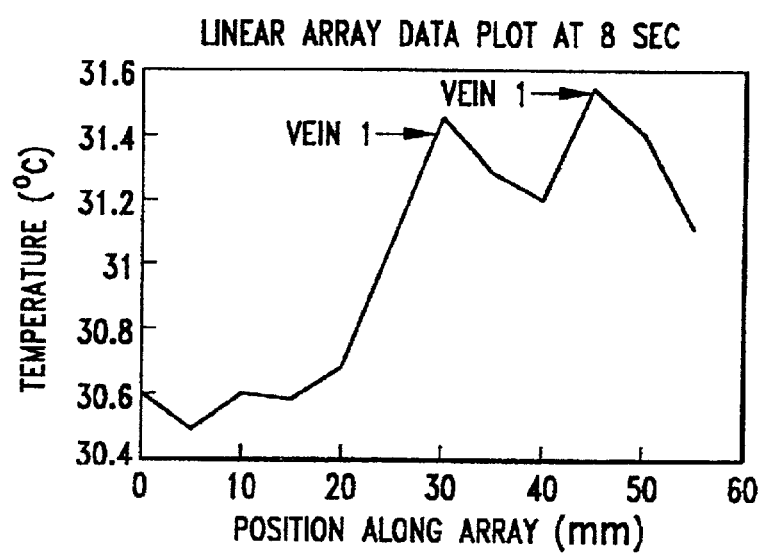
FIG. 15 is a graph plotting a temperature profile across two small veins on a forearm of a person using a surface measurement probe similar to the probe of the present invention.

The temperature profile of the biological matter which is formed may be like the one shown in FIG. 15. A plot is shown of a temperature profile measured along the surface of a volunteer, such as across two small veins on a forearm of a person, using a surface measuring probe similar to the measuring probe 12 of the present invention. The veins 1 and 2 in FIG. 15 show an increase in temperature due to an increase in blood flow. The profile in FIG. 15 was established in only 8 seconds and demonstrates the sensitivity of the measuring probe 12. A similar profile may be established for a breast tumor due to the increased blood flow to the cells of the tumor and due to the higher metabolic rates of the tumor cells when compared to normal cells.

For the foregoing description, it will be readily seen that the array of thermal sensors 22 on the measuring probe 12 of the present invention can provide added information to radiologists and may be helpful in avoiding the more severe forms of biopsy procedures. The temperature gradients sensed by the thermal sensor array may define characteristics of tumor development which distinguish benign from malignant lesions. An immediate clinical application of this technology would be to use the measuring probe to aid in accurate locating of otherwise indistinct breast tumors. In addition, it may serve to evaluate the spatial extent of treatments such as rf, microwave or focused ultrasound therapies and for use in tumor temperature studies in research. The probe would provide a temperature profile across the tumor and into the surrounding tissue, giving a quantitative measure of the progress of the therapy, which now can be done only by expensive MR temperature mapping procedures. The measuring probe also would be valuable for research in the physiology of tumors and for establishing a solid database regarding tumor temperature distributions in the breast. Such data could form the foundation for surface temperature measurement methods and could lead to improvement of early detection of breast cancer.

It is thought that the present invention and its advantages will be understood from the foregoing description and it will be apparent that various changes may be made thereto without departing from the spirit and scope of the invention or sacrificing all of its material advantages, the form hereinbefore described being merely preferred or exemplary embodiment thereof.

What is claimed is:

1. An in situ tumor temperature profile measuring probe, comprising:

an elongated rod including a pair of opposite end portions, an outer insulating layer having a plurality of spaced apart holes defined therein at one of said opposite end portions of said rod, and a common electrical input lead extending between said opposite end portions of said rod and disposed below said holes and having portions exposed at said holes, said common electrical input lead being adapted to provide an electrical input signal and said common electrical input lead of said rod is a hollow tube made of an electrically conductive material;

a plurality of spaced apart thermal sensors each formed within one of said holes of said outer insulating layer of said rod in electrical contact with said common electrical input lead of said rod, each of said thermal sensors being adapted to receive the electrical input signal from said common electrical input lead, to sense the temperature of biological matter adjacent to where said thermal sensor is placed and to produce an electrical output signal correlated to the temperature sensed; and a plurality of electrical output leads each mounted to said outer insulating layer of said rod in electrical contact with a different one of said thermal sensors and extending to the other of said opposite end portions of said rod, each of said electrical output leads being adapted to receive the electrical output signal from said one of said thermal sensors and output the electrical output signal to means for collecting the output signals and forming a temperature profile of the biological matter.

2. The probe of claim 1 in which said holes and said thermal sensors therein are arranged in a linear array in which said thermal sensors are aligned axially with respect to one another along said rod.

3. The probe of claim 1 in which each of said thermal sensors and said electrical output leads is micron-scale in size.

4. The probe of claim 1 further comprising an exterior insulating layer covering at least said electrical output leads.

5. An in situ breast temperature profile measuring probe assembly, comprising:

a measuring probe including
a pair of opposite end portions, an outer insulating layer having a plurality of spaced apart holes defined therein at one of said opposite end portions of said rod, and a common electrical input lead extending between said opposite end portions of said rod and disposed below said holes and having portions exposed at said holes, said common electrical input lead being adapted to provide an electrical input signal and said common electrical input lead of said rod of said measuring probe is a hollow tube made of a first electrically conductive material, a plurality of spaced apart thermal sensors each formed within one of said holes of and on said outer insulating layer of said rod in electrical contact with said common electrical input lead of said rod, each of said thermal sensor being adapted to receive the electrical input signal from said common electrical input lead, to sense the temperature of biological matter adjacent to where said thermal sensor is placed and to produce an electrical output signal correlated to the temperature sensed, and a plurality of electrical output leads each mounted to said outer insulating layer of said rod in electrical contact with a different one of said thermal sensors and extending to the other of said opposite end portions of said rod, each of said electrical output leads being adapted to receive the electrical output signal from said one of said thermal sensors and output the electrical output signal to means for collecting the output signals and forming a temperature profile of the biological matter;

a hollow needle insertable into biological matter and having opposite ends and an interior passageway defined through said hollow needle which is open at each of said opposite ends thereof so as to adapt said hollow needle to receive said measuring probe through said interior passageway and guide said one end portion of said rod of said measuring probe into the biological matter; and an electrical connector for providing an interface between said electrical output leads of said measuring probe and a computer, said electrical connector being adapted to receive said electrical output signals from said electrical output leads of said measuring probe and transmit the temperatures sensed by said thermal sensors of said measuring probe to the computer for collecting said output signals and forming a temperature profile of the biological matter.

6. The assembly of claim 5 in which said holes and said thermal sensors of said measuring probe are arranged in a linear array in which said thermal sensors are aligned axially with respect to one another along said rod.

7. The assembly of claim 5 in which each of said thermal sensors and said electrical output leads of said measuring probe is micron-scale in size.

8. The assembly of claim 5 in which said measuring probe also includes an exterior insulating layer covering at least said electrical output leads.

9. The assembly of claim 5 in which said hollow needle is removable from said measuring probe upon insertion of said measuring probe into the biological matter.

* * * * *